United States Patent [19]

Williamson

[11] Patent Number: 4,548,804
[45] Date of Patent: Oct. 22, 1985

[54] VISUAL-OLFACTORY HABITAT MIMIC FOR ASSESSMENT OF FRUIT FLY RESPONSE TO BEHAVIOR-MODIFYING CHEMICALS

[75] Inventor: D. Leroy Williamson, Kaneohe, Hi.

[73] Assignee: The United States of America as represented by the Secretary of Agriculture, Washington, D.C.

[21] Appl. No.: 593,058

[22] Filed: Mar. 26, 1984

[51] Int. Cl.$^4$ .............................................. A61K 49/00
[52] U.S. Cl. .......................................... 424/9; 119/15; 422/50; 428/18
[58] Field of Search .............................. 424/9; 428/18

[56] References Cited

U.S. PATENT DOCUMENTS 2,251,706  8/1941  Loewy .................................. 428/18

OTHER PUBLICATIONS

D. L. Williamson, "Olfactory Discernment of Prey by *Medetera bistriata* (Diptera: Dolichopodidae), " *Annals of the Entomological Society of America*, vol. 64, No. 3, pp. 586-589, (1971).

S. Gothilf and R. Galun, "Olfactometer and Trap for Evaluating Attractants for the Mediterranean Fruit Fly, *Ceratitis capitata*", *Phytoparasitica* 10:2, pp.79-84, (1982).

O. T. Jones, R. A. Lomer, and P. E. Howse, "Responses of Male Mediterranean Fruit Flies, *Ceratitis Capitata*, to Trimedlure in a Windtunnel of Novel Design," *Physiological Entomology* 6:175-181, (1981).

J. P. Vite' and G. B. Pitman, "Insect and Host Odors in the Aggregation of the Western Pine Beetle," *The Canadian Entomologist*, vol. 101, No. 2, pp. 113-117, (1969).

*Primary Examiner*—Sam Rosen
*Attorney, Agent, or Firm*—M. Howard Silverstein; David G. McConnell; Margaret A. Connor

[57] ABSTRACT

A method and apparatus are described which combine visual and olfactory stimuli such that behavioral responses of fruit flies to test chemicals can be readily assessed. In the method of the invention, the test chemical is placed in a chamber, air is drawn past the sample to enhance volatilization and increase the concentration of volatiles in the air, the concentrated volatiles are blown in the vicinity of a substrate which visually mimics the fruit fly host plant in a concentration sufficient to elicit a behavioral response, and the responses are observed.

17 Claims, 1 Drawing Figure

VISUAL-OLFACTORY HABITAT MIMIC FOR ASSESSMENT OF FRUIT FLY RESPONSE TO BEHAVIOR-MODIFYING CHEMICALS

BACKGROUND OF THE INVENTION

The invention relates to and has among its objects the provision of a novel method and apparatus for providing in combination visual and olfactory stimuli to fruit flies to rapidly assess behavioral responses of the flies to sample test chemicals.

Tephritid fruit flies such as the Mediterranean fruit fly [*Ceratitis capitata* (Widemann)] commonly referred to as the medfly, Oriental fluit fly (*Dacus dorsalis* Hendel), melon fly (*D. cucurbitae* Coquillet), Caribbean fruit fly [*Anastepha suspensa* (Loew)], olive fruit fly (*D. oleae* Gmelin), and Mexican fruit fly [*A. ludens* (Loew)] are among the worst pests of stonefruit and citrus fuits and vegetables and present a major threat to fruit and vegetable production. In the case of the medfly, although infestations of these flies are primarily in subtropical regions of the continent and in Hawaii, periodic invasions onto the mainland United States have resulted in great economic loss due to crop losses and costs to eradicate the pest.

Chemicals which modify the behavior of these flies, particularly those which elicit an approaching or departing response or nullify one of these responses, are important in the control of these pests. Various activities may be elicited by behavior-modifying chemicals. For example, a compound may act as an attractant, that is, produce a significant increase in number of flies attracted over those attracted by unbaited traps but that does not act as a sex attractant; sex attractant, that is, a compound that produces increased response in flies of one sex and also elicits additional responses similar to those evoked by natural sex peromonal emmissions; aggregant, that is, a compound that attracts flies of both sexes and evokes responses similar to those of natural pheromonal emissions; inhibitor, that is, a compound that reduces the number of flies attracted when exposed in a trap baited with an attractant, a phermonal extract, or live flies; disruptant, that is, a compound that interferes with the ability of insects to locate mates when the compound is disseminated throughout an area; synergist, that is, a compound that, though not attractive in itself, causes a significant increase in number of insects attracted when exposed to an attractant; and a repellant, that is, a compound which repells flies when exposed along with attractant compounds or material.

To be of any value, the behavioral response of such chemicals must be demonstrable in the normal habitat of the insect. This is particularly true in a highly evolved acalyptrate dipteran group such as tephritid fruit flies which have complex chemical communication mechanisms. Laboratory studies of fruit fly response to test chemicals have been found, in some cases, to be completely contradictory to responses by the fly in the field. For example, when the attractant compound methyl (E)-6-nonenoate (MEN) was tested in the laboratory, it attracted female medflies; in contrast, MEN was solely attractive to male medflies in the field.

Another important criteria in the field testing of chemicals which elicit a behavioral response of fruit flies is the ability to observe responses such as courtship, mating, feeding, defense of territory, and other behavioral patterns, in addition to merely quantifying numbers of flies attracted or captured. This is particularly important in the study of tephritid fruit flies because many of these flies, notably those of economic importance, naturally initiate aggregations by males where attraction, courtship, and mating with female flies are performed. Distant chemical communication is accomplished from leks, i.e., territories within host plant communities where the intricate male displays and signaling are conducted, often away from ovipositional sites subsequently selected by females.

Presently, no method or apparatus exists for the rapid assessment in the field of fruit fly response to behavior-modifying chemicals. Devices to measure olfactory response of fruit flies in the laboratory are well known. These include small to walk-in sized cage-type olfactometers in which traps containing candidate compounds are suspended from a rotating motor-driven wheel to provide rotational presentation of test materials or which provide wind-tunnel effects. These devices have the problems that laboratory response may not be indicative of field response, that artifacts may be introduced, and that primary measurement is number of flies trapped or contained. Observations of numbers of test chemicals in the trephritid natural habitat is impractical because of the time required to locate difficult to find mating sites for testing. Conventional devices to test behavior-modifying chemicals in the field comprise traps which measure the number of flies trapped or contained. While these devices are useful for detecting, monitoring, or mass-trapping flies, other responses such as mating, courtship, and the like are not elicited with these traps. Additionally, conventional traps have to be distributed over a large area and replicated several times to obtain a meaningful response and thus require weeks of time and manpower.

Two-dimensional visual cues such as host plant foliage pressed between plexiglass sheets, a tree-shaped pattern drawn on plywood, and colors and shapes similuating host fruit contrasts have been tested against tephritids to provide insight into visual stimuli; however, no method or device has fulfilled the need for a rapid way to assess behavioral responses such as courtship, mating, feeding, and the like of fruit flies in the field in response to behavior-modifying chemicals.

SUMMARY OF THE INVENTION

I have discovered a novel method and apparatus which combines visual and olfactory stimuli in a unique manner to mimic the habitat of fruit flies such that responses of the flies in the field to behavior-modifying chemicals can be rapidly assessed. Surprisingly, behavioral responses such as courtship, mating, lekking behavior, feeding, territory establishment, in addition to attracting or trapping, occur with the use of my invention.

The method of the invention comprises placing the behavior-modifying test chemical sample in a chamber, drawing air past the sample to enhance volatilization and increase the concentration of sample volatiles in the air, blowing the concentrated volatiles in the vicinity of a substrate which visually mimics the fruit fly host plant in a manner such that a continuous emission of the test sample volatiles is dispersed around the host plant mimic in a concentration sufficient to elicit a behavioral response, and observing fruit fly response.

The apparatus of the invention comprises a chamber for holding the chemical sample to be tested; means for drawing air past the sample to enhance volatilization of the sample and concentrate the sample volatiles in the air; a substrate which visually mimics the plant host of the fruit fly, e.g., foliage, and means for blowing the volatile-laden air in the vicinity of the visual plant host mimic to provide a continuous emission of volatiles to be dispersed around the foliage in a concentration sufficient to elicit a behavioral response.

This combination of a continuous emission of olfactory stimulating chemical to provide an emission gradient of volatiles in sufficient concentration to direct the insect's flight response over distance in combination with a substrate which visually mimics the insect's natural plant host provides a visual-olfactory habitat mimic for rapid field assessment of behavioral responses of fruit flies to behavior-modifying chemicals. In addition to attraction or trapping, responses such as courtship, mating, territory establishment, feeding, and lekking are observed with my invention.

In accordance with this discovery, it is an object of the invention to provide a visual-olfactory habitat mimic and method of using the same wherein the behavioral responses of tephritid fruit flies to test chemicals in the field can be easily and rapidly assessed without the investment of time and expense of searching for natural mating sites.

It is also an object of the invention to provide means for assessing test chemicals in the field to maximize the assessment of true insect responses, that is, responses which would occur in the insect's natural habitat and minimize the production of artificial responses that occur in laboratory testing.

It is another object of the invention to provide a system wherein natural insect responses in the field to test chemicals, in addition to trapping or containment, such as attraction of insects to the preselected site, feeding, courtship, mating, defense of territory, aggregation, lekking, repelling, and stimulation can be rapidly assessed. Such a system is needed to accelerate research of effective control means and to evaluate pest management systems.

Another object is to supply visual and olfactory stimuli to tephritid fruit flies to allow study of behavior; bioassay of pheromones, lures, and attractants; and assessment of insect quality of laboratory-reared, sterilized flies.

It is also an object of the invention to provide a monitoring system for sterile insect release programs.

Other objects and advantages of the invention will become readily apparent from the ensuing description.

DESCRIPTION OF THE PREFERRED EMBODIMENTS

Figure 1:
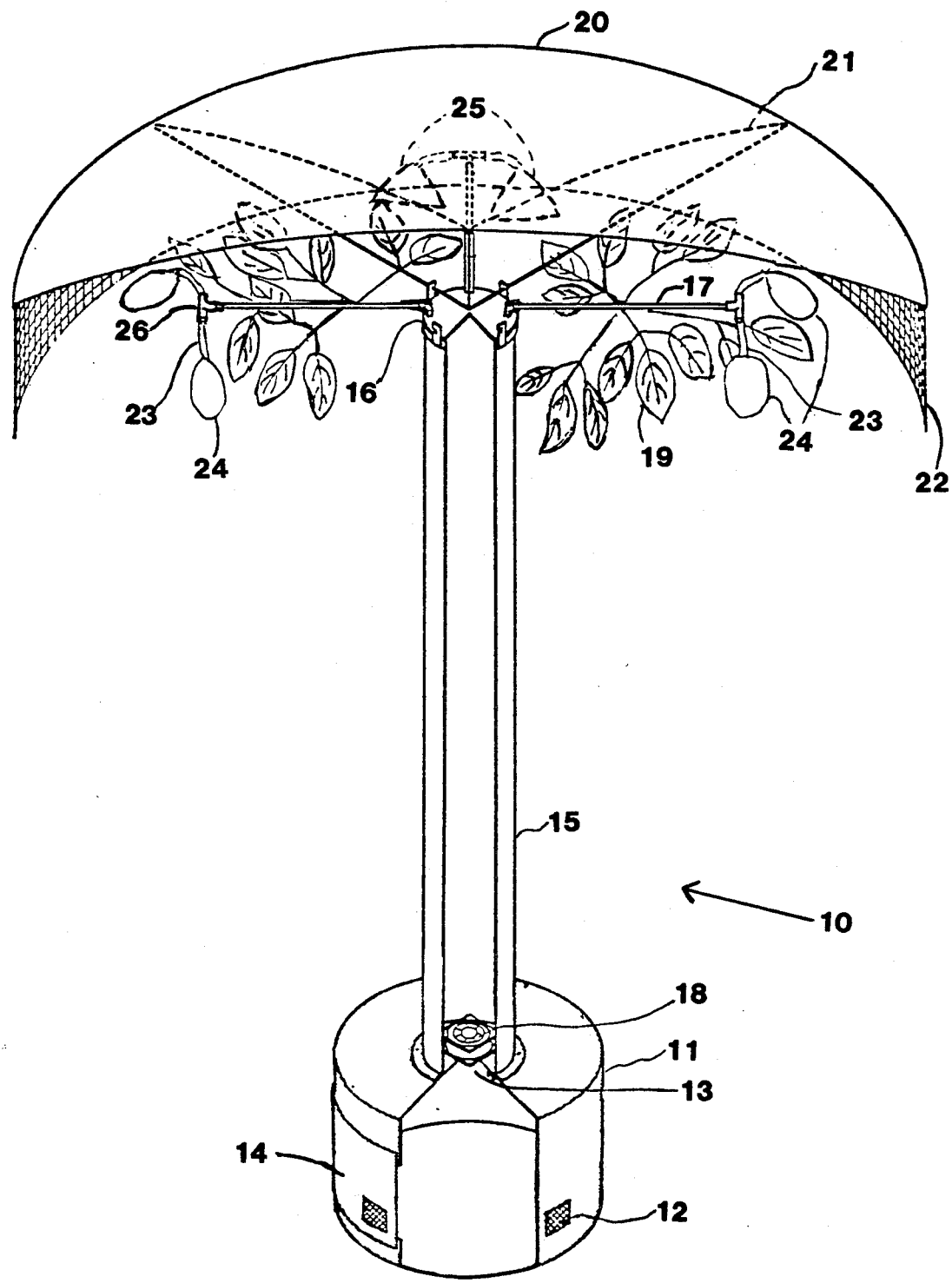
FIG. 1 is a cutaway view of the visual-olfactory apparatus of the invention.

The apparatus and method of the invention will next be described in detail with reference to the attached drawing.

FIG. 1 depicts visual-olfactory habitat mimic 10, which includes chamber 11 for holding the test chemical sample to be assessed. Chamber 11 is provided with air intake ports 12, air outlet port 13, and closable door 14. Pipe stem 15 is fixedly attached at one end to chamber 11 at opening 13 and closed at the other end by end plate 16. Distribution pipes 17 which communicate with pipe 15 are attached to end plate 16. Fan 18 is located at the base of pipe 15 adjacent to opening 13 in chamber 11. The substrate which visually mimics the insect host plant comprises foliage 19 which is supported by distribution pipes 17. Additional visual stimuli is optionally provided by perforated plastic lemon 24 attached to the exit port of pipe 17 through tubing 23. Where desirable, traps may be added such as trap 25 attached to the exit port of pipe 17 through tubing 23. Removable canopy 20 is supported by support members 21 attached to end plate 16. Capture screen 22, which surrounds foliage 19 and distribution pipes 17, is attached to canopy support members 21.

In the method of the invention as described with reference to FIG. 1, the test chemical sample is placed in chamber 11 and door 14 closed. Fan 18 draws air into chamber 11 through ports 12 and around the test sample to increase volatilization of the sample and blows the volatile-laden air through pipe 15 and out distribution pipes 17 where it is dispersed in the vicinity of foliage 19, lemon 24, and trap 25.

The size of chamber 11 is not critical; however, it should be large enough to conveniently hold the test sample and small enough so that air taken in through intake ports 12 surrounds the sample to enhance volatilization of the sample and concentrate the sample volatiles such that the volatile-laden air exiting distribution pipes 17 in the vicinity of the host plant visual mimic substrates (e.g., foliage 19 and lemon 24) is of sufficient concentration to elicit a behavioral response in the insect group whose behavior is to be assessed. Air intake ports 12 must provide sufficient surface opening in chamber 11 in relation to the exit openings of pipes 17 so that air intake into chamber 11 exceeds air exhausted through distribution pipes 17. Screening of the ports is suggested to prevent intake of solid particles or insects into the chamber. Chamber 11 can be made of any rigid material such as aluminum, stainless steel, or rigid plastic. The painting of chamber 11 black may be desirable to aid volatilization of the test sample and provide upward convection of the volatiles in the chamber. Fan 18 can be powered by any number of ways such as by a portable gasoline engine, electric generator, photovoltaic power source, or electric outlet. The amount of air/second moved by fan 18 around the test sample and out pipes 17 must be that sufficient to provide a continuous flow of volatile-laden air in the vicinity of the host plant visual mimic in a concentration sufficient to elicit a behavioral in the insect group being studied, particularly to direct the insect's flight response over distance.

Pipe 15 and end plate 16 are made of any rigid material. The size of pipe 15 must be sufficient to allow sufficient passage of volatile-laden air to pipes 17 and provide support for all items attached to the upper end of pipe 15 under wind or weather conditions that may occur. Distribution pipes 17 disperse the emission of olfactory volatiles in the vicinity of the host plant visual mimic to thereby provide a gradient of emitted volatiles around the visual mimic, the gradient being strongest closest to the emission source and decreasing at increasing distances away from the device. To carry out the invention, the concentration of volatiles emitted must be sufficient to elicit the desired insect response. It is preferred that the volatile-laden air circumferentially surround the device in the vicinity of the foliage to provide a substantially uniform concentration gradient of volatiles around the device in the vicinity of the foliage. This increases the number of insects affected by the test chemical and allows detection of the travel path of the insects responding. A convenient arrangement of distribution pipes 17 is at 90 degree angles as shown in FIG. 1. Pipes 17 may be made of any rigid material to which artificial foliage may be attached and from which traps can be suspended.

The type and location of the host plant visual mimic is critical. Tephritid fruit flies are very affected by variables in visual stimuli, such as light shining through leaves, possibly color of plant host substrate and the like. It has been found that to achieve responses to olfactory stimuli, in addition to attraction to the stimuli, that the plant host visual mimic should be visually similar to the insect's natural habitat. It has been found that foliage as shown in FIG. 1 presents fruits flies with the required visual stimuli. It is advantageous that the foliage be artificial so that olfactory stimuli inherently present in natural foliage not interfere with the measurement of the response to the test chemical. A suitable material for artificial leaves is green silk as it resembles natural foliage and does not become as hot as do plastic leaves. The location of the foliage should be near the emission ports and attached so that volatiles pass over or in close proximity to this substrate. In the study of medfly response, it has been found that the attachment of perforated artificial yellow plastic lemons to one or more distribution pipe outlets causes a primary site of landing response and easiest observation because of contrasting background to the insect's body color. Such addition is not critical to the practice of the invention however. Traps 25 may also be attached to the distribution pipes as shown in FIG. 1, where trapping of the insects is desired.

Removable canopy 20 is not essential to the invention, however it is advantageous to hold in volatiles around the foliage, shield the apparatus from excessive sunlight, prevent metal parts from becoming too hot, and to protect the foliage, traps, and other parts from the elements.

Capture screen 22 which circumferentially surrounds the device in the vicinity of the foliage is not essential, but is useful when studying numbers of flies attracted, particularly where low populations of flies are present. When the apparatus is used as a trap, the capture screen, when coated with a sticky substance, increases efficiency of capture and also readily shows, by distribution of flies on the screen, the direction from which the flies are responding. The screen can also be used to study the behavior of fruit fly parasites which congregate around the screen waiting for fly eggs to be laid.

The particular combination of visual and olfactory stimuli described is essential to cause the highly evolved tephritid insect group to not only come to the device but to display a multitude of behavioral responses such as courtship, mating, lekking, feeding, and defense of territory, the knowledge of which is important to the acceleration of provision of effective control and pest management systems. The concentration and distribution of a continuous emission of olfactory volatiles in the vicinity of the host plant visual mimic is critical to the practice of the invention. The concentration must be sufficient to elicit a response from the insects. A convenient way to determine the critical requirements is to set the chamber size, air flow, fan speed, and distribution pipe size and array in a manner such that a predetermined response to fruit flies is achieved with a reference behavior-modifying chemical such as the medfly attractant, trimedlure, (tert-butyl, 4(or 5)-chloro-2-methylcyclohexanecarboxylate). Responses of subsequently tested samples are then denoted with reference to the control chemical. Because variables such as plant host mimic composition and condition, climate, and the like are standardized for each comparison test, responses can be easily assessed as opposed to conventional trapping procedures which require time consuming repetitive testing over a large area to get meaningful results. While the invention can be used indoors, it finds particular use for testing behavior-modifying chemicals under field conditions.

EXAMPLE

The method and apparatus of the invention are described in further detail in the following illustrative examples which were carried out in Waimanalo, Hawaii.

EXAMPLE 1

Referring to FIG. 1, chamber 11 which was made of galvanized metal which had been painted black had the following dimensions: height, 31 cm; inner diameter, 45 cm; and width of door opening, 30 cm. Located in chamber 11 were four screened intake ports (12) which were each 5 cm by 5 cm. Air outlet port 13 at the top of chamber 11 had an inner diameter of 7.5 cm. Pipe stem 15 had an inner diameter of 15 cm and a length of 150 cm. End plate 16 covered the top of pipe stem 15. Four copper tubing distribution pipes (17) attached to end plate 16 and communicating with pipe stem 15 were located at 90 degree angles from one another. Each had an inner diameter of 1.0 cm and a length of 39 cm. "T" joints 26 attached to the exit end of pipes 17 were matched for tubing size. A total of four plastic yellow lemons, two per set, were attached to tubing 23, with pairs opposite each other as shown in FIG. 1. Pairs of triangular-shaped, 1-mm thick cardboard traps, 9.5×9.5×9.5 by 12.5 cm, were attached to tubing 23 on the other two distribution pipes with the flexible tube inserted through a hole at mid-point of the trap length. (Placement of the second pair of traps 15 not shown in FIG. 1, but would be projecting out of the drawing). Each trap had a cardboard insert, 16 by 9.5 cm, coated with a sticky substance to capture flies on the floor of the trap. Green silk foliage was attached to pipes 17 with metal hose clamps to form a natural habitat appearance. Canvas-covered, circular canopy, 1.5 m in diameter mounted on a wire frame was attached to support members 21. Extra trapping surface (22) made of a 0.6 cm mesh galvanized wire screen was attached to the canopy rim with wire "s" hooks and ends attached with two metal spring clamps. A Pee Wee Boxer Fan 18, driven by 110VAC, was located at the base of stem 15 with the direction of air-flow pointed upward.

Four samples—trimedlure (TML); IN 645.1, a test attractant supplied by M. Jacobson, USDA Biologically Active Natural Products Laboratory; TML+IN 645.1, and a control (water)—were tested. One apparatus was used for each sample and each apparatus was rotated hourly with the adjacent one to eliminate positional effects. The test period consisted of three 4-hour periods. The sample size was 0.05 ml for each except for the sample of TML+IN 645.1 which consisted of 0.025 ml of each combined. Each sample was placed on a cotton dental wick and positioned in chamber 11 on a wire pedestal and door 14 closed. Motor 13 was turned on so that air flowed through ports 12 and around the sample, up pipe 15 and out pipes 17. Flow rate fluctuated from 2–5 ml/min depending on gusts of wind around the base chamber. Responses of fruit flies to the sample were observed and measured. The results are tabulated in Table I. In addition to trapping, courtship behavior and male calling were observed with TML and IN 645.1. Testing of these samples using conventional trapping procedures took weeks.

TABLE I

| Compound | No. male medflies trapped | | | | | |
|---|---|---|---|---|---|---|
| | Hourly rotated Position | | | | | |
| | 1 | 2 | 3 | 4 | Total | x ± S.E. |
| IN 645.1 | 23 | 28 | 4 | 33 | 88 | 22.0 ± 12.7 |
| TML | 10 | 8 | 8 | 7 | 33 | 8.3 ± 1.3 |
| TML + IN 645.1 | 1 | 1 | 5 | 2 | 9 | 2.3 ± 1.9 |
| Control | 2 | 3 | 0 | 0 | 5 | 1.3 ± 1.5 |

EXAMPLE 2

The following example was carried out with TML and medflies with and without plant host mimics foliage 19 and lemons 24 to illustrate the effect of the mimics on fruit fly response. Tests with and without canopy 20 and screen 22 were also compared. One apparatus was used per test configuration. Responses of fruit flies were observed and measured. The results are tabulated in Table II. As can be seen from the results, when the plant host mimics were removed flies were attracted to the traps, but no behavioral responses such as mating or male calling were observed. Addition of screen 22 increased numbers of flies trapped.

TABLE II

| Olfactometer Configuration | Exposure period (hr) | No. male medflies trapped | | | | No. medflies observed during exposure period | | |
|---|---|---|---|---|---|---|---|---|
| | | Total | | Per hour | | | | |
| | | Delta traps | Sticky screen | Delta traps | Sticky screen | Calling | Unmated | Mating pairs |
| A. Plant mimics, screen, canopy, traps | 8.5 | 36 | 250 | 4.2 | 29.4 | — | — | — |
| B. Plant mimics, screen, canopy traps | | 41 | 254 | 4.8 | 29.9 | — | — | — |
| A. Plant mimics, canopy, traps | 12 | 123 | — | 11.2 | — | 70 | 7 | 10 |
| B. Canopy, traps[1] | | 190 | — | 17.3 | — | 0 | 0 | 0 |
| A. Plant mimics, traps | 12 | 123 | — | 13.7 | — | 107 | 10 | 3 |
| B. Traps[1] | | 29 | — | 3.6 | — | 0 | 0 | 0 |

[1]Not in accordance with the invention but used for comparison purposes.

It is understood that the foregoing detailed description is given merely by way of illustration and that modification and variations may be made therein without departing from the spirit and scope of the invention.

Having thus describe my invention, I claim:

1. A method for assessment of tephritid fruit flies to behavior-modifying test chemical samples, which comprises placing the test chemical sample in a chamber, drawing air past the sample to enhance volatilization and increase the concentration of volatiles in the air in the chamber, blowing the volatile-laden air in the vicinity of a substrate which visually mimics the fruit fly plant host to provide a concentration of sample volatiles in the vicinity of the substrate to elicit a behavioral response in fruit flies in the vicinity of the substrate, and observing fruit fly response in response to the chemical sample.

2. The method as described in claim 1 wherein said plant host mimic comprises artificial foliage.

3. The method as described in claim 1 further comprising placing a canopy over said plant host mimic.

4. The method as described in claim 1 further comprising placing a screen circumferentially around said plant host mimic.

5. The method as described in claim 1 further comprising placing a trap in the vicinity of said plant host mimic.

6. The method as described in claim 1 further comprising placing a capture screen in the vicinity of said plant mimic.

7. An apparatus for the assessment of fruit flies to behavior-modifying test chemical samples, which comprises a substrate which visually mimics the fruit fly plant host, a chamber for holding the chemical sample to be tested, pipe means connected at one end to said chamber and supporting said substrate at another end, and fan means for drawing air past the sample to enhance volatilization and concentrate the sample volatiles in the air and for blowing the volatile-laden air through the pipe means to the vicinity of the substrate to provide a continuous emission of volatiles around the substrate in a concentration sufficient to elicit a behavioral response in fruit flies in the vicinity of the substrate in response to the chemical sample.

8. The apparatus as described in claim 7 wherein said plant host mimic comprises artificial foliage.

9. The apparatus as described in claim 8 wherein said plant host mimic further comprises plastic lemons.

10. The apparatus as described in claim 7 which further comprises a canopy located above said plant host mimic.

11. The apparatus as described in claim 7 which further comprises a screen surrounding the apparatus in the vicinity of said plant host mimic.

12. The apparatus as described in claim 7 which further comprises traps for fruit flies.

13. The apparatus as described in claim 7 wherein said chamber for holding the sample to be tested is black.

14. The apparatus of claim 7 which further includes a test chemical sample located inside said chamber.

15. The apparatus of claim 7 wherein said chamber has air intake ports and wherein said pipe means comprises: (a) a pipe connected to the chamber at one end and (b) distribution pipes connected to said pipe at another end of said pipe and wherein said distribution pipes provide support for said substrate.

16. The apparatus as described in claim 15 which further comprises traps for fruit flies.

17. The apparatus as described in claim 8 which further comprises a canopy located above said foliage.

* * * * *